United States Patent
Reid et al.

(10) Patent No.: US 9,271,922 B2
(45) Date of Patent: Mar. 1, 2016

(54) DEPILATORY CREAM COMPOSITION

(75) Inventors: Sylvie Reid, Hull (GB); Anne Tindal, Hull (GB); Philippe Valcasara, Hull (GB)

(73) Assignee: RECKITT & COLMAN (OVERSEAS) LIMITED, Slough, Berkshire (GB)

( * ) Notice: Subject to any disclaimer, the term of this patent is extended or adjusted under 35 U.S.C. 154(b) by 0 days.

(21) Appl. No.: 14/002,785

(22) PCT Filed: Feb. 29, 2012

(86) PCT No.: PCT/GB2012/050454
§ 371 (c)(1),
(2), (4) Date: Oct. 29, 2013

(87) PCT Pub. No.: WO2012/120277
PCT Pub. Date: Sep. 13, 2012

(65) Prior Publication Data
US 2014/0143960 A1    May 29, 2014

(30) Foreign Application Priority Data
Mar. 4, 2011  (GB) .................................. 1103677.9

(51) Int. Cl.
| | | |
|---|---|---|
| *A61K 8/891* | (2006.01) | |
| *A61K 8/37* | (2006.01) | |
| *A61K 8/39* | (2006.01) | |
| *A61K 8/41* | (2006.01) | |
| *A61K 8/46* | (2006.01) | |
| *A61Q 19/04* | (2006.01) | |
| *A61K 8/86* | (2006.01) | |
| *A61K 8/898* | (2006.01) | |
| *A61K 8/34* | (2006.01) | |
| *A61K 8/73* | (2006.01) | |
| *A61Q 9/04* | (2006.01) | |

(52) U.S. Cl.
CPC . *A61K 8/891* (2013.01); *A61K 8/34* (2013.01); *A61K 8/342* (2013.01); *A61K 8/375* (2013.01); *A61K 8/39* (2013.01); *A61K 8/416* (2013.01); *A61K 8/46* (2013.01); *A61K 8/463* (2013.01); *A61K 8/731* (2013.01); *A61K 8/86* (2013.01); *A61K 8/898* (2013.01); *A61Q 9/04* (2013.01); *A61Q 19/04* (2013.01)

(58) Field of Classification Search
CPC combination set(s) only.
See application file for complete search history.

(56) References Cited

U.S. PATENT DOCUMENTS

| | | | |
|---|---|---|---|
| 5,645,825 A | * | 7/1997 | Hillebrand et al. ............. 424/73 |
| 6,200,554 B1 | * | 3/2001 | Yeoh et al. ................. 424/70.12 |
| 6,479,043 B1 | | 11/2002 | Tietjen et al. |
| 6,503,517 B1 | | 1/2003 | Mohammadi et al. |
| 2004/0219118 A1 | | 11/2004 | Slavtcheff et al. |
| 2007/0299410 A1 | | 12/2007 | Eknoian et al. |
| 2008/0138304 A1 | | 6/2008 | Biggs et al. |

FOREIGN PATENT DOCUMENTS

| | | |
|---|---|---|
| CA | 2354829 A1 | 2/2003 |
| EP | 0089710 A1 | 9/1983 |
| FR | 2924928 A1 | 6/2009 |
| GB | 2327190 A * | 1/1999 |
| WO | 2008110745 A2 | 9/2008 |
| WO | WO 2008110745 A2 * | 9/2008 |

OTHER PUBLICATIONS

McKay, Amodimethicone and other amine-functionalized silicones, Jul. 1, 2007.*
Stearyl dimethicone-International Journal of Toxicology, vol. 22 Supplement, 2003, pp. 11-35.*
International Search Report and Written Opinion; dated Dec. 13, 2013; prepared by Alain Diebold.

* cited by examiner

*Primary Examiner* — Robert A Wax
*Assistant Examiner* — Melissa Mercier
(74) *Attorney, Agent, or Firm* — Troutman Sanders LLP; Ryan A. Schneider; Troy S. Kleckley

(57) ABSTRACT

A depilatory cream composition comprising •a depilatory active; and, •a conditioning complex; wherein the conditioning complex comprises: •one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain; •a silicone or an optionally branched alkane containing at least 12 carbon atoms; •an ethoxylated fatty alcohol and/or ethoxylated fatty ester with an HLB value of 13 or above; and, •a conditioning agent •water.

21 Claims, No Drawings

DEPILATORY CREAM COMPOSITION

CROSS-REFERENCE TO RELATED APPLICATIONS

This application is a US National Stage of International Application No. PCT/GB2012/050454, filed 29 Feb. 2012, which claims the benefit of GB 1103677.9, filed 4 Mar. 2011, both herein fully incorporated by reference.

This invention relates to a depilatory composition with the additional effect of conditioning the skin, and the methods of use and manufacture thereof.

Compositions for removing superfluous body hair are known and are of various types. One type of composition requires initial heating before being applied to the skin in a generally molten state. It is then allowed to solidify before being removed from the skin together with unwanted hair. This is known in the art as epilation, as the hairs are uprooted from the skin.

Another type of composition is in the form of a cream, which can be applied to the skin at room temperature. The cream includes a substance that degrades hair keratin. Conventionally, the compositions are applied to the skin where unwanted hair is present, then left in place for a predetermined time to allow the keratin in the hair to become degraded. The composition along with degraded hair is then removed from the skin, usually with a tool such as a sponge or wipe or spatula. Such compositions are known in the art as depilatory compositions.

Depilatory compositions act to remove the hair by chemically weakening/destroying the hair, thereby allowing the hair to be washed off the body e.g. in the shower. A frequent result of this, however, are undesirable side effects on the skin as a result of the harsh depilatory active ingredients (alkaline pH). If a standard moisturiser is used in the composition to try to counteract this effect, there is a resultant loss in efficacy of the depilatory active owing to the occlusive effect of the moisturiser hindrering penetration of the active into the hair.

There is a need therefore for a depilatory composition which also provides beneficial effects to the skin treated without any detrimental effect on the performance of the depilatory active.

According to a first aspect of the present invention, there is described a depilatory cream composition comprising
a depilatory active; and,
a conditioning complex;
wherein the conditioning complex comprises:
  one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain;
  a silicone or an optionally branched alkane containing at least 12 carbon atoms;
  an ethoxylated fatty alcohol and/or ethoxylated fatty ester with an HLB value of 13 or above;
  a conditioning agent; and
  water.

The depilatory agent is a substance capable of degrading keratin. The depilatory agent, according to the present invention, may include a mixture of one or more depilatory agents. Preferred depilatory agents are sulfhydryl compounds, meaning a compound having an —S—H group. Suitable sulfhydryl depilatory agents include but are not limited to the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically- and/or pharmaceutically acceptable salts of any of the foregoing compounds.

Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof. More preferred sulfhydryl compounds include thioglycolic acid, cysteine, glutathione and N-acetyl-L-cysteine and cosmetically- and/or pharmaceutically acceptable salts thereof. The most preferred sulfhydryl compound is thioglycolic acid and cosmetically- and/or pharmaceutically-acceptable salts thereof. As used herein, "cosmetically- and/or pharmaceutically-acceptable salts" of the sulfhydryl compounds include, but are not limited to alkali metal salts, e.g., sodium, lithium, rubidium and potassium salts; alkaline earth metal salts, e.g., magnesium, calcium and strontium salts; non-toxic heavy metal salts, e.g., aluminum salts and zinc salts; boron salts; silicon salts; ammonium salts; trialkylammonium salts, e.g., trimethylammonium and triethylammonium; and tetralkylonium salts.

Preferred cosmetically- and/or pharmaceutically-acceptable salts of the sulfhydryl compound include sodium, potassium and calcium salts. Most preferred salts of the sulfhydryl compound are potassium and calcium salts.

Suitably, the composition comprises from 1 to 20% by weight, preferably from 2 to 10% by weight, more preferably from 2 to 8% by weight, especially from 3 to 5% by weight of depilatory agent expressed as the acid form of the depilatory agent. For example, it is preferred that the composition comprises potassium thioglycolate at pH12.4, this is not expressed as potassium thioglycolate, but as the equivalent weight of thioglycolic acid.

Optionally, the composition includes an accelerator that will accelerate the keratin degradation reaction. Suitable accelerators include urea, thiourea, dimethyl isosorbide, ethoxydiglycol and methyl propyl diol. Preferably the accelerator is urea or methyl propyl diol. The composition according to the invention preferably comprises from 5% to 15% by weight, more preferably 7% to 10% by weight of an accelerator.

It is particularly preferred for the composition to comprise a pH regulator to assist in activating the depilatory agent, particularly when the depilatory agent is a sulfhydryl compound. Preferably the quantity and type of pH regulator is chosen to maintain the pH of the composition at a value greater than 5, preferably greater than 7, more preferably from 8 to 13, most preferably from 10 to 12.9, especially from 12 to 12.7. For example, by ensuring that the pH is about 12.1 to 12.7, depilation can occur within about 5 minutes, as desired by the user, without causing undue irritation. Higher pH levels can lead to irritation problems with some users.

The pH regulator preferably is in the continuous aqueous phase (between the hydrophobic particles) when present. Examples of the pH regulator include arginine (especially L-arginine), silicates (e.g. sodium or potassium silicate), calcium hydroxide and polyethyleneimine. Mixtures of pH regulators may be used. It is particularly preferred for the pH regulator also to include calcium hydroxide in an amount from 2 to 4% by weight of the composition. The pH regulator may be dissolved in the aqueous phase of the composition or may be present as solid particles dispersed throughout the composition.

Compositions according to the invention comprise hydrophobic particles distributed as an emulsion (an oil-in-water emulsion) in an aqueous continuous phase which is a liquid at 25° C. By aqueous it is meant that the continuous phase comprises at least 50% by weight in total of water, preferably 70% by weight or more based on the total weight of the continuous phase. The amount of water in the composition as a whole will typically be from 40% to 95% by weight of the composition.

In a further aspect of the first embodiment of the present invention, there is described a depilatory cream composition substantially as hereinbefore described wherein the glycol carboxylate is selected from the condensation products of an alkylene-mono-ol or an alkylenediol with a carboxylic acid.

In a further aspect of the first embodiment of the present invention, there is described a depilatory cream composition substantially as hereinbefore described wherein the alkylenediol is ethylene glycol, 1,3-propanediol or 1,4-butanediol.

In a further aspect of the first embodiment of the present invention, there is described a depilatory cream substantially as hereinbefore described wherein the carboxylic acid is a monocarboxylic acid of molecular formula $R^3CO_2H$ wherein $R^3$ is an optionally unsaturated $C_{6-28}$ hydrocarbon, preferably $C_{12-20}$, most preferably $C_{16-18}$. In an especially preferred embodiment, $R^3$ is a $C_{18}$ hydrocarbon.

In a further aspect of the first embodiment of the present invention, there is described a depilatory cream composition substantially as hereinbefore described wherein the glycol carboxylate is ethylene glycol distearate.

In a further aspect of the first embodiment of the present invention, there is described a depilatory cream substantially as hereinbefore described wherein the silicone is selected from the group consisting of dimethicone, cyclomethicone, cyclohexa/penta/tetra/tri-siloxanes, polydimethicone, polydimethylsiloxane and mixtures of there of. Additionally, the silicone may be added as a mixture with a cationic compound, typical such mixtures being amodimethicone, trideceth-12 and cetrimonium chloride. Particularly preferred are aminofunctional siloxanes, and an especially preferred silicone is amodimethicone.

In a further aspect of the first embodiment of the present invention, there is described a depilatory cream substantially as hereinbefore described wherein the silicone is amodicomethicone.

In a further aspect of the first embodiment of the present invention, there is described a depilatory cream substantially as hereinbefore described which further comprises stearyl dimethicone.

In a further aspect of the first embodiment of the present invention, there is described a depilatory cream composition substantially as hereinbefore described wherein the ethoxylated fatty alcohol is selected from the group consisting of ceteth-2, ceteth-10, ceteth-20, cetoleth-10, ceteareth-12, ceteareth-20, ceteareth-25, isoceteth-20, steareth-2, steareth-10, steareth-20, steareth-21, oleth-2, oleth-3, oleth-5, oleth-10, oleth-20, laureth-4, laureth-9, laureth-12, laureth-23, ceteareth-20, C12-13 pareth-3, C12-13 pareth-4, C12-13 pareth-7, C12-13 pareth-12, C12-15 pareth-9, C14-15 pareth-13, and mixtures thereof.

In a further aspect of the first embodiment of the present invention, there is described a depilatory cream composition substantially as hereinbefore described wherein the ethoxylated fatty alcohol is selected from the group consisting of ceteth-10, laureth-12, steareth-10, and mixtures thereof.

In a further aspect of the first embodiment of the present invention, there is described a depilatory cream substantially as hereinbefore described wherein the ethoxylated fatty ester is selected from the group consisting of PEG-35 castor oil, PEG-40 hydrogenated castor oil, PEG-40 castor oil, Laneth-15, PEG-8 laurate, PEG-6 caprylic/capric glycerides.

It is preferred that the ethoxylated fatty alcohol or the ethoxylated fatty ester has an HLB value of at least 13, calculated according to the methodology of Griffin (J Society of Cosmetic Chemists 5 (1954), 259).

In a further aspect of the first embodiment of the present invention, there is described a depilatory cream composition substantially as hereinbefore described wherein the conditioning agent is selected from the group consisting of quarternary ammonium compounds, ethoxylated glycerol phosphate, $C_n$ alcohols, $C_n$ ethoxylated alcohol phosphates, $C_n$ propoxylated alcohol phosphates, and $C_n$ alcohol phosphates (wherein n is between 6 and 28, preferably between 12 and 20, more preferably between 16 and 18, especially 16), or a mixture thereof.

Preferably when the conditioning agent is a quarternary compound, it is selected from the group consisting of Polyquaternium-X/quaternium-X family+Lauryldimonium Hydroxypropyl Hydrolyzed Wheat Protein (and) Lauryldimonium Hydroxypropyl Hydrolyzed Wheat Starch, Lauryldimonium Hydroxypropyl Hydrolyzed Soy Protein, Lauryldimonium Hydroxypropyl Hydrolyzed Collagen, Cocodimonium Hydroxypropyl Hydrolyzed Collagen, Steardimonium Hydroxypropyl Hydrolyzed Collagen, Lauryldimonium Hydroxypropyl Hydrolyzed Keratin, Cocodimonium Hydroxypropyl Hydrolyzed Keratin, Cocodimonium Hydroxypropyl Silk Amino Acids, Cocodimonium Hydroxypropyl Hydrolyzed Milk Protein, C10-40 Isoalkylamido-propylethyldimonium Ethosulfate (and) Dipropylene Glycol, Behenalkonium Chloride, behentrimonium methosulfate (and) C10-40 Isoalkylamido-propylethyldimonium Ethosulfate (and) Cetyl alcohol, behentrimonium Chloride, Cetrimonium Chloride, Dicetyldimonium Chloride, PEG-3 Dioleoylamidoethylmonium Methosulfate, Stearalkonium Chloride, cetrimonium chloride, dipalmitoylethyl Hydroxyethylmonium Methosulfate, Hydroxycetyl Hydroxyethyl Dimonium Choloride, Distearoylethyl Hydroxyethylmonium Methosulphate, Dicocoylethyl Hydroxyethylmonium Methosulphate, Distearyldimonium chloride. Preferably the quarternary compound is C10-40 isoalkylamidopropyl ethyldimonium ethosulfate (& dipropylene glycol) or Polyquaternium-10 (cationic hydroxyethyl cellulose) or Behentrimonium methosulfate (& cetyl alcohol) or ceteth-10 phosphate (& cetyl alcohol).

In a further aspect of the first embodiment of the present invention, there is described a depilatory cream composition substantially as hereinbefore described wherein the $C_n$ alcohol phosphate is selected from the group consisting of dicetyl phosphate, ceteth-10 phosphate, glycereth-26 phosphate and PPG-5 ceteth-10 phosphate.

In a further aspect of the first embodiment of the present invention, there is described a depilatory cream composition substantially as hereinbefore described which comprises 1 to 40 weight % conditioning complex, preferably 20 to 40 wt %, more preferably 25-35 wt %.

In a further aspect of the first embodiment of the present invention, the amount of water comprised in the conditioning complex is from 5 to 30% by weight, preferably from 10 to 25% by weight, more preferably from 15 to 20% by weight, where these percentages are based on the composition as a whole.

In a second embodiment of the present invention, there is described the use of a conditioning complex substantially as hereinbefore described comprising a glycol carboxylate, a silicone, an ethoxylated fatty alcohol, a conditioning agent and water improve the skin feel of a depilatory cream composition.

In a third embodiment of the present invention, there is described a method of manufacture of a composition substantially as hereinbefore described comprising the following steps:
- melt together the components of the conditioning complex at a temperature of at least 80° C.;
- emulsify this melt in water under high shear;
- cool down the mixture at least to 35° C. and add any remaining ingredients; and,
- mix and emulsify the mixture until it thickens.

In a further aspect of the third embodiment of the present invention, there is described a method of depilation comprising:
- applying a composition substantially as hereinbefore described to the skin;
- allowing the composition a residence time on the skin in order to degrade the hairs on the skin's surface;
- at the end of the residence time removing the composition and depilated hairs from the skin by rinsing the skin with water and using a removal tool e.g. cloth.

EXAMPLES

The invention will now be further described with the help of the following non-limiting examples.

Base formulae 1 and 2 (components shown in % w/w):

| Component | Formula 1 | Formula 2 |
|---|---|---|
| Water (1) | 37.615 | 37.615 |
| Water (2)* | 18.0* | 18.0* |
| Potassium Thioglycolate | 5.7 | 5.7 |
| Water | 7.2 | 7.2 |
| Urea | 8.0 | 8.0 |
| Ethylene Glycol Distearate* | 3.0* | 3.0* |
| Polyoxyethylene (10) Cethyl Ether* | 4.0* | 6.0* |
| Conditioning agent* | 0.5* | 0.5* |
| Calcium Hydroxide | 3.56 | 3.56 |
| Talc | 2.0 | 2.0 |
| Amodimethicone/Cyclotetrasiloxane* | 1.5* | 1.5* |
| Potassium Hydroxide Water | 1.0 | 1.0 |
| Sorbitol | 1.0 | 1.0 |
| Glycerin | 1.0 | 1.0 |
| CI 45380 (3) Propylene Glycol CI 77891 | 0.6 | 0.6 |
| Magnesium Trisilicate Water | 0.5 | 0.5 |
| Parfum Linalool | 0.4 | 0.4 |
| Lithium Magnesium Sodium Silicate | 0.2 | 0.2 |
| Sodium Gluconate | 0.1 | 0.1 |
| Water | 0.1 | 0.1 |
| Propylene Glycol Dicaprylate/Dicaprate Nelumbo Nucifera Flower Extract Xanthan Gum Phenoxyethanol Methylparaben Ethylparaben Butylparaben Propylparaben Isobutylparaben Water Acrylic Polymer | 4.0 | 2.0 |
| Hydrated Silica Water | 0.025 | 0.025 |

Components marked with an asterisk (*) part of the conditioning complex.

The conditioning agent components are:

| Example 1 | Example 2 |
|---|---|
| Cationic Hydroxyethyl Cellulose | Behentrimonium Methosulfate |
| Water | Cetyl Alcohol |
| Sodium Acetate | Butylene Glycol |
| Sodium Chloride | Amines, C16-C22 |
| Isopropanol | Alkyldimethyl |

In order to prepare the composition, the following steps are carried out:
- melt together the components of the conditioning complex, apart from water(2), at a temperature of at least 80° C.;
- emulsify this melt in water(2) under high shear;
- cool down the mixture at least to 35° C. and add any remaining ingredients; and,
- mix and emulsify the mixture until it thickens.

Alternatively, the process can be carried out as follows:
- in a separate vessel melt together the components of the conditioning complex, apart from water(2), at a temperature of at least 80° C.;
- emulsify this melt in water(2) under high shear;
- in the main vessel add any remaining ingredients at room temperature and, mix and emulsify the mixture until it thickens; then
- add the conditioning complex emulsion to the main vessel and mixture under agitation to complete the formula.

The invention claimed is:

1. A depilatory cream composition comprising:
a depilatory active; and
a conditioning complex;
wherein the conditioning complex comprises:
one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain;
one of a silicone or branched alkane containing at least 12 carbon atoms;
one or both of an ethoxylated fatty alcohol and an ethoxylated fatty ester with an HLB value of 13 or above;
a conditioning agent; and
water,
wherein the silicone is an aminofunctional siloxane.

2. The depilatory cream composition according to claim 1, wherein the depilatory agent is selected from the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically and/or pharmaceutically acceptable salts thereof.

3. The depilatory cream composition according to claim 1 comprising from 1 to 20% by weight of depilatory agent expressed as the acid form of the depilatory agent.

4. The depilatory cream composition according to claim 1, wherein the glycol carboxylate is selected from the condensation products of an alkylene-mono-ol or an alkylenediol with a carboxylic acid.

5. The depilatory cream composition according to claim 1, wherein the glycol carboxylate comprises an alkylenediol selected from the group consisting of ethylene glycol, 1,3-propanediol and 1,4-butanediol.

6. The depilatory cream composition according to claim 1, wherein the glycol carboxylate comprises an alkylenediol with a carboxylic acid, wherein the carboxylic acid is a monocarboxylic acid of molecular formula $R^3CO_2H$ wherein $R^3$ is an optionally unsaturated $C_{6-28}$ hydrocarbon.

7. The A depilatory cream composition according to claim 6, wherein $R^3$ is a $C_{18}$ hydrocarbon.

8. The depilatory cream composition according to claim 7, wherein the glycol carboxylate is ethylene glycol distearate.

9. The depilatory cream composition according to claim 1, wherein the silicone is amodimethicone.

10. The depilatory cream composition according claim 1 wherein the ethoxylated fatty alcohol is selected from the group consisting of ceteth-2, ceteth-10, ceteth-20, cetoleth-10, ceteareth-12, ceteareth-20, ceteareth-25, isoceteth-20, steareth-2, steareth-10, steareth-20, steareth-21, oleth-2, oleth-3, oleth-5, oleth-10, oleth-20, laureth-4, laureth-9, laureth-12, laureth-23, ceteareth-20, C12-13 pareth-3, C12-13 pareth-4, C12-13 pareth-7, C12-13 pareth-12, C12-15 pareth-9, C14-15 pareth-13, and mixtures thereof.

11. The depilatory cream composition according claim 1 wherein the ethoxylated fatty ester selected from the group consisting of PEG-35 castor oil, PEG-40 hydrogenated castor oil, PEG-40 castor oil, Laneth-15, PEG-8 laurate, and PEG-6 caprylic/capric glycerides.

12. The depilatory cream composition according to claim 1, wherein the conditioning agent is selected from the group consisting of quarternary ammonium compounds, ethoxylated glycerol phosphate, $C_n$ alcohols, $C_n$ ethoxylated alcohol phosphates, $C_n$ propoxylated alcohol phosphates, and $C_n$ alcohol phosphates (wherein n is between 6 and 28), or a mixture thereof.

13. A depilatory cream composition comprising:
a depilatory agent; and
a conditioning complex;
wherein the conditioning complex comprises:
one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain;
one of a silicone or branched alkane containing at least 12 carbon atoms;
one or both of an ethoxylated fatty alcohol and an ethoxylated fatty ester with an HLB value of 13 or above;
a conditioning agent; and
water,
wherein the conditioning agent is selected from the group consisting of a quaternary compound and a $C_n$ alcohol phosphate,
wherein the quarternary compound is selected from the group consisting of Polyquaternium-X/quaternium-X family+Lauryldimonium Hydroxypropyl Hydrolyzed Wheat Protein (and) Lauryldimonium Hydroxypropyl Hydrolyzed Wheat Starch, Lauryldimonium Hydroxypropyl Hydrolyzed Soy Protein, Lauryldimonium Hydroxypropyl Hydrolyzed Collagen, Cocodimonium Hydroxypropyl Hydrolyzed Collagen, Steardimonium Hydroxypropyl Hydrolyzed Collagen, Lauryldimonium Hydroxypropyl Hydrolyzed Keratin, Cocodimonium Hydroxypropyl Hydrolyzed Keratin, Cocodimonium Hydroxypropyl Silk Amino Acids, Cocodimonium Hydroxypropyl Hydrolyzed Milk Protein, C10-40 Isoalkylamido-propylethyldimonium Ethosulfate (and) Dipropylene Glycol, Behenalkonium Chloride, behentrimonium methosulfate (and) C10-40 Isoalkylamidopropylethyldimonium Ethosulfate (and) Cetyl alcohol, behentrimonium Chloride, Cetrimonium Chloride, Dicetyldimonium Chloride, PEG-3 Dioleoylamidoethylmonium Methosulfate, Stearalkonium Chloride, cetrimonium chloride, dipalmitoylethyl Hydroxyethylmonium Methosulfate, Hydroxycetyl Hydroxyethyl Dimonium Choloride, Distearoylethyl Hydroxyethylmonium Methosulphate, Dicocoylethyl Hydroxyethylmonium Methosulphate, and Distearyldimonium chloride, and
wherein the $C_n$ alcohol phosphate is selected from the group consisting of dicetyl phosphate, ceteth-10 phosphate, glycereth-26 phosphate and PPG-5 ceteth-10 phosphate.

14. The depilatory cream composition according to claim 1 comprising 1 to 40 weight % conditioning complex.

15. The depilatory cream composition according to claim 1, wherein the amount of water comprised in the conditioning complex is from 5 to 30% by weight based on the composition as a whole.

16. A method of manufacturing a composition comprising:
melting together the components of the conditioning complex at a temperature of at least 80° C.;
emulsifying the melt in water under high shear;
cooling down the mixture at least to 35° C.; and
mixing and emulsifying the mixture until it thickens,
wherein the composition is a depilatory cream composition comprising:
a depilatory agent; and
a conditioning complex;
wherein the conditioning complex comprises:
one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain;
one of a silicone or branched alkane containing at least 12 carbon atoms;
one or both of an ethoxylated fatty alcohol and an ethoxylated fatty ester with an HLB value of 13 or above;
a conditioning agent; and
water.

17. A method of depilation comprising:
applying the composition according to claim 1 to the skin;
allowing the composition a residence time on the skin in order to degrade hairs on the skin's surface; and
at the end of the residence time, removing the composition and depilated hairs from the skin by rinsing the skin with water and using a removal tool or cloth.

18. The depilatory cream composition according to claim 1 comprising from 3 to 5% by weight of depilatory agent expressed as the acid form of the depilatory agent.

19. A depilatory cream composition comprising:
a depilatory agent; and
a conditioning complex;
wherein the conditioning complex comprises:
one or more of: a glycol carboxylate, a dialkyl ether of formula $R^1$—O—$R^2$ wherein $R^1$ and $R^2$, independently of one another, represent linear or branched alkyl and/or alkenyl groups having from 6 to 28 carbon atoms; and, an aliphatic alkyl mono-alcohol having at least 12 carbon atoms in the alkyl chain;
one of a silicone or branched alkane containing at least 12 carbon atoms;

one or both of an ethoxylated fatty alcohol and an ethoxylated fatty ester with an HLB value of 13 or above;
a conditioning agent; and
water,
wherein the glycol carboxylate comprises an alkylenediol with a carboxylic acid, wherein the carboxylic acid is a monocarboxylic acid of molecular formula $R^3CO_2H$ wherein $R^3$ is an optionally unsaturated $C_{16-18}$ hydrocarbon.

20. The depilatory cream composition according to claim 1 comprising 25-35 weight % conditioning complex.

21. The depilatory cream composition according to claim 1, wherein the amount of water comprised in the conditioning complex is from 15 to 20% by weight based on the composition as a whole.

* * * * *